US006663856B1

(12) United States Patent
Giordano

(10) Patent No.: US 6,663,856 B1
(45) Date of Patent: *Dec. 16, 2003

(54) METHOD OF INHIBITING CANCER CELL GROWTH USING A VECTOR EXPRESSING PRB2/P130

(75) Inventor: Antonio Giordano, Philadelphia, PA (US)

(73) Assignee: Thomas Jefferson University, Philadelphia, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 86 days.

(21) Appl. No.: 09/089,194

(22) Filed: Jun. 2, 1998

Related U.S. Application Data
(60) Provisional application No. 60/048,297, filed on Jun. 2, 1997.

(51) Int. Cl.$^7$ .......................... A61K 48/00; A61K 35/00
(52) U.S. Cl. ........................ 424/93.2; 424/93.1; 514/44
(58) Field of Search ..................... 514/44; 435/325; 424/277.1, 93.1, 93.21, 93.2

(56) References Cited

U.S. PATENT DOCUMENTS

| 5,457,049 A | 10/1995 | Giordano ............... 435/252.33 |
| 5,496,731 A | 3/1996 | Xu et al. |
| 5,596,079 A | 1/1997 | Smith et al. |

FOREIGN PATENT DOCUMENTS

| JP | 0 666 270 | 8/1995 |

OTHER PUBLICATIONS

Xu et al. Cancer Res. vol. 56, pp. 2245–2249, 1996.*
Davis et al. Curr. Op. Onc., vol. 8, pp. 499–508, 1996.*
Miller et al., Targeted vectors for gene therapy, 1995, FASEB, vol. 9 pp. 190–199.*
Crystal, Transfer of genes to humans: Early lessons and Obstacles to success, 1995, Science, vol. 270 pp. 404–410.*
Deonarain. Ligand–targetd receptor–mediated vectors for gene delivery, 1998, Exp. Opin. Ther. Patents, vol. 8 pp. 53–69.*
Claudio et al., Mutations in the retinoblastoma–related gene RB2/p130 in lung tumors and suppression of tumor growth in vivo by retrovirus–mediated gene transfer, 2001, Cancer Research vol. 60 pp. 372–382.*
Ross et al. Human Gene Therapy, vol. 7, pp. 1781–1790, Sep. 1996.*
Verma et al. Nature, vol. 389, p. 239–242, Sep. 18, 1997.*
Feldman et al, Fundamental & Clinical Pharmacology, vol. 9, pp. 8–16, 1995.*

Orkin et al. "Report and Recommendations of the Panel to Assess the NIH investment in Research on Gene Therapy", Dec. 7, 1995.*
Baldi et al. Proc. Natl. Acad. Sci., vol. 93, pp. 4629–4632, May 1996.*
Claudio et al. Cancer Research, vol. 54, pp. 5556–5560, Nov. 1, 1994.*
Gura Science, vol. 278, pp. 1041–1042, Nov. 7, 1997.*
Vieweg et al. Cancer Investigation, vol. 13, pp. 193–201, 1995.*
Alley et al., "Feasibility of Drug Screening with Panels of Human Tumor Cell Lines Using a Microculture Tetrazolium Assay[1]", 1988 Cancer Res. 48:589–601.
Baldi et al., "Genomic structure of the human retinoblastoma–related Rb2/p130 gene", 1996 *Proc. Natl. Acad. Sci.* 93:4629–4632.
Baldi et al., "The Rb2/p130 Gene Product Is a Nuclear Protein Whose Phosphorylation Is Cell Cycle Regulated", 1995 *J. Cell Biochem.* 59:402–408.
Baldi et al., "Differential Expression of the Retinoblastoma Gene Family Members pRb/p105, p107, and pRb2/p130 in Lung Cancer[1] ", Clinical Cancer Res. 1996 7:1239–1245.
Bargmann et al., "The neu oncogene encodes an epidermal growth factor receptor–related protein", 1986 *Nature* 319:226–230.
Barnes et al., "Gene Therapy and Ovarian Cancer: A Review", *Obstetrics and Gynecology* 1997 89:145–155.
Claudio et al., "Functional Analysis of pRb2/p130 Interaction with Cyclins[1]", 1996 *Cancer Res.* 56:2003–2008.
Claudio et al., "p130/pRb2 Has Growth Suppressive Properties Similar to yet Distinctive from Those of Retinoblastoma Family members pRb and p107[1]", 1994 Cancer Res. 54:5556–5560.
Claudio et al., "Intraarterial Chemotherapy Through Carotid Transposition in Advanced Head and Neck Cancer", 1990 *Cancer* 65:1465–1471.
Claudio et al., "Factors affecting response and survival in advanced head and neck cancers treated with intraarterial chemotherapy", 1992 *Reg. Cancer. Treat.* 4:180–187.
Coussens et al., "Tyrosine Kinase Receptor with Extensive Homology to EGF Receptor Shares Chromosomal Location with neu Oncogene", 1985 *Science* 230:1132–1139.
Davis et al., "Current progress in the gene therapy of cancer", *Current Opinion in Oncology* 1996 8:499–508.
DeCaprio et al., "The Product of the Reinoblastoma Susceptibility Gene Has Properties of a Cell Cycle Regulatory Element", 1989 *Cell* 58:1085–1095.
De Luca et al., A Unique Domain of pRb2/p130 Acts as an Inhibitor of Cdk2 Kinase Activity, *J. Biol. Chem.* 1997 272:20971–20974.

(List continued on next page.)

Primary Examiner—Michael Wilson
(74) Attorney, Agent, or Firm—William J. McNichol, Jr.; Nanda P.B.A. Kumar

(57) ABSTRACT

Methods of inhibiting growth of cancer cells and treating cancer in a patient by administration of a vector expressing pRb2/p130 are provided.

9 Claims, No Drawings

OTHER PUBLICATIONS

Eck and Wilson *Goodman & Gilman's The Pharmacological Basis of Therapeutics* 1996, Chapter 5.

Giordano et al., "Cell Cycle Regulation of Histone H1 Kinase Activity Associated with the Adenoviral Protein E1A", *Science* 1991 253:1271–1275.

Gossen, M. and Bujard, H., "Tight control of gene expression in mammalian cells by tetracycline–responsive promoters", *Proc. Natl. Acad. Sci. USA* 1992 89:5547–5551.

Gunning et al., "Isolation and Characterization of Full–Length cDNA Clones for Human α–, β, and y–Actin mRNAs: Skeletal but Not Cytoplasmic Actins Have an Amino–Terminal Cysteine that Is Subsequently Removed", 1983 *Mo. Cell. Biol.* 3:787–795.

Guy et al., "Expression of the neu protooncogene in the mammary epithelium of transgenic mice induces metastatic disease", 1992 *Proc. Natl. Acad. Sci.* 89:10578–10582.

Hanania et al., Recent Advances in the Application of Gene Therapy to Human Disease, *Am. Jour. Med.* 1995 99:537–552; Johnson et al. *J. Am. Acad. Derm.* 1995 32(5):689–707.

Huang, H–J. et al., "Suppression of the Neoplastic Phenotype by Replacement of the RB Gene in Human Cancer Cells", 1988. *Science* 242:1563–1566.

Huttner et al., "NA–mediated Gene Transfer without Carrier DNA", 1981 *J. Cell. Biol.* 91:153–156.

Johnson et al., Current therapy for cutaneous melanoma, *J. Am. Acad. Derm.* 1995 32(5):689–707.

Kern et al., C–erbB–2 Expressions nd Codon 12 K–ras Mutations Both Predict Shortened Survival for Patients with Pulmonary Adenocarcinomas, 1994 *J. Clin. Invest.* 93:516–520.

Martelli et al., Nuclear localization and signalling activity of phosphoinositidase $C^\beta$ in Swiss 3T3 cells, *Nature* 1992 358:242–244.

Mayol et al. "Cloning of a new member of the retinoblastoma gene family (pRb2) which binds to the E1A transforming domain", 1993, *Oncogene* 8:2561–2566.

Neri et al., "Nuclear Scaffold Proteins Are Differently Sensitive to Stabilizing Treatment by Heat or Cu++", *J. Histochem. Cytochem.* 1997 45:295–305.

Park et al., Amplification, Overexpression, and Rearrangement of the erbB–2 Protooncogne in Primary Human Stomach Carcinomas, 1989 *Cancer Res.* 49:6605–6609.

Pupa et al., MacrophageInfiltrate and Prognosis in c–erbB–2–Overexpressing Breast Carcinomas, 1996 *J. Clin. Oncol.* 14:85–94.

Raj, G.V. et al., "Characterization of glioma cells derived from human polyomavirus–induced brain tumors in hamsters", 1995. *Int. J. Oncol.* 7:801–808.

Rilke et al., Prognostic Significance of Her–2/NEU Expression In Breast Cancer And Its Relationship to Other Prognostic Factors, 1991 *Int. J. Cancer* 49:44–49.

Roth and Cristiano, "Gene Therapy for Cancer: What Have We Done and Where Are We Going", *J. Natl. Canc. Inst.* 1997 89(1):21–39.

Sang et al., "Generation of Site–Directed Mutagenesis by Extralong, High–Fidelity Polymerase Chain Reaction", *Anal. Biochem.* 1996 233:142–144.

Shockett, P. et al., "A modified tetracycline–regulated system provides autoregulatory, inducible gene expression in cultured cells and transgenic mice", 1995.

Slamon et al., "Studies of the HER–2/neu Proto–oncogene in Human Breast and Ovarian Cancer", 1989 *Science* 244:707–712.

Tagliabue et al., "Selection of Monoclonal Antibodies Which Induce Internalization and Phosphorylation of p185 her21 And Growth Inhibition of Cells with HER2/NEU Gene Amplification", 1991 *Int. J.*.

Wessel, D. and Flugge, "Method for the Quantitative Recovery of Protein in Dilute Solution in the Presence of Detergents and Lipids", U.I. Anal. Biochem. 1984 138:14–143.

Yeung et al., "The retinoblastoma–related gene, RB2, maps to human chromosome 16q12 and rat chromosome 19", 1993 *Oncogene* 8:3465–3468.

Zacksenhaus et al., A Bipartite Nuclear Localization Signal in the Reinoblastoma Gene Product and Its Importance for Biological Activity, Mol. Cell Biol. 1993 13:4588–4599.

Zhu et al., "Inhibition of cell proliferation by p107, a relative of the retinoblastoma protein", 1993 *Gene Develop.* 7:1111–1125.

Gu et al., "Inhibition of CDK2 Activity In Vivo By An Associated 20K Regulatory Subunit", *Nature*, vol. 366 (6465), p. 707–710, 1993.

Susini et al., "Expressions of the Retinoblastoma–Related Gene Rb2/p130 Correlates with Clinical Outcome in Endometrial Cancer", *Journal of Clinical Oncology*, vol. 16, No. 3, pp. 1085:1093 1998.

Baldi et al., The Rb2/p130 Gene Product is a Nuclear Protein Whose Phosphorylation is Cell Cycle Regulated; *Journal of Cellular Biochemistry*, 59(3): p. 402–408, 1995.

Paggi et al., "Retinoblastoma Protein Family in Cell Cycle and Cancer: A Review", *Journal of Cellular Biochemistry*, 62(3): p. 418–430, 1996.

Eck et al., "Treatment of Advanced CNS Maligancies With The Recombinant Adenovirus H5.010RSVTK: A Phase I Trial", *Human Gene Therapy*, 7:1465–1482, 1996.

Kiess et al., "Expressions and Activity of the Retinoblastoma Protein (pRB) Family Proteins, p107 and p130, during $L_6$ Myoblast Differentiation", *Cell Growth & Differentiation*, 6(10) p 1287–1298, 1995.

Hannon et al., "Isolation of the Rb–related p130 through its interaction with CDK2 and cyclins", *Genes & Development* 7:2378–2391, 1993.

Wilson et al., "Gene Therapy of cystic Fibrosis Lung Disease Using E1 Deleted Adenoviruses: A Phase 1 Trial", *Human Gene Therapy*, 7:2378–2391, 1993.

Tursz et al., "Phase I Study of a recombinant advenovirus–mediated gene transfer in lung cancer patients", *Journal of the National Cancer Institute*, vol. 88, No. 24, 1996.

Bellon et al., "Aerosol Administration of a Recombinant Adenovirus Expression CFTR To Cystic Fibrosis Patients: A Phase 1 Clinical Trial", *Human Gene Therapy*, 8:15–25, 1997.

Gahery–Segard et al., "Phase I Trial of Recombinant Adenovirus Gene Transfer In Lung Cancer", *J. Clin. Invest.*, vol. 100, No. 9, p. 2218–2226, 1997.

Sterman et al., "Adenovirus–Mediated Herpes Simplex Virus Thymidine Kinase/Ganciclovir Gene Therapy In Patients with Localized Malignancy; Results of a Phase I Clinical Trial in Malignant Mesothelimoa" *Human gene therapy*, 9: 1093–1092, 1998.

Roth et al., "Gene Therapy for Non–Small Cell Lung Cancer: A Preliminary Report of a Phase I Trial of Adenoviral P53 Gene Replacement", *Seminars In Oncology*, vol. 25, No. 3, Suppl pp. 33–37, 1998.

* cited by examiner

SEQUENCE LISTING

```
<160> NUMBER OF SEQ ID NOS: 11

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: A linker
      oligonucleotide sequence to change a restriction
      site in a vector

<400> SEQUENCE: 1
ggccggggga tccccc                                                       16

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 2
gtccttcggg cacctc                                                       16

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 3
tcaccgagct gcaagaac                                                     18

<210> SEQ ID NO 4
<211> LENGTH: 21
```

```
<212> TYPE: DNA
<213> ORGANISM: Artificial Sequence
<220> FEATURE:
<223> OTHER INFORMATION: Description of Artificial Sequence: Primer

<400> SEQUENCE: 4
aggtcctatc accaagggtg t                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 5
gcttagttac ttcttcaagg c                                              21

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 6
gagaaagtta atatcctagc tg                                             22

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 7
gtgaatggtc catatataaa tca                                            23

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 8
tggtttagca cacctcttca c                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 9
gcttagcaca aaccctgttt c                                              21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 10
```

```
ctgagctatg tgcatttgca                                          20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 11
aaggctgctg ctaaacagat                                          20
```

METHOD OF INHIBITING CANCER CELL GROWTH USING A VECTOR EXPRESSING PRB2/P130

This application claims priority to provisional application 60/048,297, filed Jun. 2, 1997.

INTRODUCTION

This invention was made in the course of research sponsored by the National Institutes of Health. The U.S. Government may have certain rights in this invention.

BACKGROUND OF THE INVENTION

Cancer is a genetic disease that results from multiple genomic changes. These changes ultimately lead to the malfunction of cell cycle machinery and finally to autonomous cell proliferation. Neoplastic transformation involves four types of genes: oncogenes, tumor-suppressor genes, mutator genes, and apoptotic genes. Different types of cancer can involve alteration of any one or any combination of these genes.

In order for genomic alterations to lead to effects on cell proliferation, they must in some way affect the normal processes that control the cell cycle. The cell then becomes an autonomous unit capable of replicating without reliance on the external environment that normally signals a cell when to divide, to arrest, to differentiate, or to apoptose. Therefore, neoplastic development is ultimately a disturbance in either the positive regulators of the cell cycle (proto-oncogenes), the negative regulators (tumor suppressor genes), and/or apoptotic regulators of cell growth and proliferation. To develop more effective strategies for identification and treatment of various forms of cancer the mechanisms that operate within the cell cycle and how they might interlink, become disturbed, and be regulated must be considered.

Major advances in molecular biology, biochemistry and tumor biology have changed the way research scientists and clinicians conceptualize the management and treatment of cancer. Proteins that mediate cell cycle control are now being elucidated (e.g., p53 nuclear protein), while DNA technology provides ready access to the genes that control the events. Direct targeting of these proteins for either delivery or modification by conventional pharmacologic agents is difficult because of the size, inaccessibility, and complexity of the proteins themselves. Manipulation of the genes that control expression of these proteins, i.e., gene therapy, however, overcomes these barriers by selectively introducing recombinant DNA into tissues thereby leading to alterations in the expression of the biologically active protein in tissues. This in turn leads to alterations in cell function.

Gene therapy is now accepted as a therapeutic tool for treating diseases such as cancer. See, for example, Eck and Wilson Goodman & Gilman's *The Pharmacological Basis of Therapeutics* 1996, Chapter 5. Gene therapy for treatment of cancer has been the focus of multiple clinical trials approved by the National Institutes of Health Recombinant DNA Advisory Committee, many of which have demonstrated successful clinical application (Hanania et al. *Am. Jour. Med.* 1995 99:537–552; Johnson et al. *J. Am. Acad. Derm.* 1995 32(5) :689–707; Barnes et al. *Obstetrics and Gynecology* 1997 89:145–155; Davis et al. *Current Opinion in Oncology* 1996 8:499–508; Roth and Cristiano *J. Natl. Canc. Inst.* 1997 89(1):21–39). An important factor for success when employing alterations of gene expression as a therapeutic strategy is to begin by establishing a sound scientific basis for manipulation of that gene and its gene product.

The focus of gene therapy strategies for cancer has been not only on altering growth of a malignancy but also on diagnosis and prognosis of patients' disease. For diagnostic and prognostic methods, markers for cell cycle regulatory proteins are being developed. A goal of these methods is to decrease the morbidity and mortality of various forms of cancer by promoting earlier recognition and intervention. Early detection of tumors allows for use of more effective treatments such as immunotherapy which requires a low tumor burden ($<10^9$ cells). Further, more efficient classification of tumors based on molecular alterations in oncogenes, tumor suppressor genes, apoptotic genes, and/or mutator genes allows for less subjective interpretation by pathologists. This in turn leads to better choices of therapy.

Many forms of malignancy have been linked to mutations in the tumor suppressor gene known as retinoblastoma, or Rb. The retinoblastoma gene which encodes the nuclear protein p53 is the most frequently altered gene in cancer, where defects in the function of this suppressor gene lead to unregulated cell proliferation. Studies have led to the identification of an additional member of the Rb family, p107 which has also been labeled as a tumor suppressor gene. Cellular proliferation has been shown to be triggered by growth factor receptor activation as well as being controlled by cell cycle regulators such as Rb and p107 (DeCaprio et al. 1989 *Cell* 58:1085–1095; Zhu et al. 1993 *Gene Develop.* 7:1111–1125).

A third gene, Rb2/p130, has also been identified which is structurally and functionally related to both the Rb gene itself and p107 (Baldi et al. *Proc. Natl. Acad. Sci. USA* 1996 93:4629–4632). All three share several regions of identity that constitute a functional domain known as the "pocket region". This "pocket region" is involved in binding to the transforming proteins from DNA tumor viruses, such as the E1A protein from adenovirus, as well as binding to cellular transcription factors such as E2F. Therefore, the "pocket" plays a critical role in protein-protein interactions.

pRb2/p130 has been cloned and identified based upon binding to the E1A transforming domain (Mayol et al. 1993, *Oncogene* 8:2561–2566). Further, the genomic structure of the human retinoblastoma-related Rb2/p130 gene which provides a molecular basis for understanding the transcriptional control of the gene itself and for delineating potential Rb2/p130 mutations in human tumors was recently disclosed (Baldi et al. 1996 *Proc. Natl. Acad. Sci.* 93:4629–4632). The Rb2/p130 gene has been mapped to human chromosome 16q12.2 (Yeung et al. 1993 *Oncogene* 8:3465–3468); deletions of this chromosome have been found in several human neoplasias including breast, hepatic, ovarian, and prostatic cancer. Accordingly, pRb2/p130 is believed to be a tumor suppressor gene in human carcinoma.

Rb2/p130 has been shown to have a role as regulator in cell cycle function. For example, Baldi et al. have shown that phosphorylation of the Rb2/p130 gene product is regulated in a cell cycle dependent manner (Baldi et al. 1995 *J. Cell. Biochem.* 59:402–408), in the same way that the phosphorylation of Rb is cell cycle dependent (DeCaprio et al. 1989 *Cell* 58:1085–1095). Further, the growth suppressive properties of the gene product of Rb2/p130 have been shown to be specific for the $G_1$ phase in similar fashion to pRb and p107 (Claudio et al. 1996 *Cancer Res.* 56:2003–2008). The gene product of Rb2/p130 has been shown to arrest growth in human tumor cell lines in a manner similar to the other members of the Rb family (i.e., pRb and p107). However, this protein also inhibits proliferation in a glioblastoma cell line that is resistant to the growth suppressant effects of both pRb and p107 (Claudio et al. 1994 *Cancer Res.* 54:5556–5560). Accordingly, pRb2/p130 has similar yet distinctive growth suppressive properties from pRb and p107 (Claudio et al. 1994 Cancer Res. 54:5556–5560).

It has now been found that pRb2/p130 affects tumor cell growth. The tumorigenicity mediated by a specific oncogene, c-erbB-2 (HER2\neu) is affected. Further, it has been found that pRb2/p130 affects tumor cell growth in cells not linked to expression of c-erb-2, as well as in tumor cells that are deficient in pRb2/p130 and cells that contain pRb2/p130. Compositions which comprise pRb2/p130 have been identified that can be incorporated into a vector and transfected into tumor cells to inhibit growth of the cells.

SUMMARY OF THE INVENTION

An object of the present invention is to provide a composition comprising a vector expressing pRb2/p130 and a pharmaceutically acceptable carrier.

Another object of the present invention is to provide a method of inhibiting growth of tumor cells which comprises transfecting tumor cells with a plasmid comprising pRb2/p130.

Another object of the present invention is to provide a method for diagnostic screening of tumor cells to identify those tumors best treated by administration of a plasmid comprising pRb2/p130.

DETAILED DESCRIPTION OF THE INVENTION

The present invention relates to compositions and methods for inhibiting tumorigenicity. The compositions and methods relate to reversing the tumorigenicity of pRb2/p130 negative cancer cells and cells induced by proto-oncogenes such as c-erbB-2, as well as cells that express pRb2/p130. In the present invention, a composition comprising a vector expressing pRb2/p130 is transfected into tumor cells so that growth of the tumor cells is inhibited.

Carcinomas of the breast, ovary, lung, and stomach each have been linked to the presence and expression of a specific human proto-oncogene known as c-erbB-2, also known as HER2/neu (Slamon et al. 1989 *Science* 244:707–712; Park et al. 1989 *Cancer Res.* 49:6605–6609; Rilke et al. 1991 *Int. J. Cancer* 49:44–49; Guy et al. 1992 *Proc. Natl. Acad. Sci.* 89:10578–10582; Kern et al. 1994 *J. Clin. Invest.* 93:516–520; Pupa et al. 1996 *J. Clin. Oncol.* 14:85–94). The c-erbB-2 (HER2\neu) oncogene encodes a 185,000 dalton epidermal growth factor receptor-related transmembrane protein ($p185^{HER2}$) that has intrinsic tyrosine kinase activity (Bargmann et al. 1986 *Nature* 319:226–230; Coussens et al. 1985 *Science* 230:1132–1139). Overexpression of this protein correlates with aggressive disease and a poor prognosis (Rilke et al. 1991 *Int. J. Cancer* 49:44–49; Kern et al. 1994 *J. Clin. Invest.* 93:516–520; Pupa et al. 1996 *J. Clin. Oncol.* 14:85–94). Specifically, amplification of this gene has been associated with breast cancer (Slamon et al. 1989. *Science* 244:707–712), ovarian cancer (Slamon et al. 1989. *Science* 244:707–712), and primary stomach carcinoma (Park et al. 1989. *Cancer Res.* 49:6605–6609). Expression of c-erbB-2 has also been suggested to be related to the metastatic qualities of tumor growth based upon studies in a mammary tumor model in mice (Guy et al. *Proc Natl. Acad. Sci. USA* 1992 89:10578–10582) and lung carcinomas from humans (Kern et al. *J. Clin. Invest.* 1994 93:516–520). Thus, c-erbB-2 expression plays a role in the development and progression of several forms of carcinoma in both animals and humans.

It has now been found that introduction of the pRb2/p130 cDNA into human cancer cells (those specifically linked to c-erbB-2 expression) results in reduction of growth rate and colony formation in vitro and suppresses tumor growth in vivo in athymic mice, despite the expression of $p185^{HER2}$ receptor capable of autophosphorylation. In addition, studies in tumor cell lines not specifically linked to c-erb-2 expression have shown that pRb2/p130 expression inhibits tumor cell growth. Studies were performed in three different types of tumor cells, ovarian tumor cells, lung tumor cells, and brain tumor cells, as well as in patients with endometrial cancer.

Studies in Ovarian Tumor Cells

Plasmid containing the coding sequence for pRb2/p130 under the transcriptional control of CMV promoter and an empty vector (mock transfection) were successfully transfected into SKOV3 cells. Northern blot analysis demonstrated an increase in pRb2/p130 mRNA levels in the transfected clones as compared with mock and wild-type SKOV3 cells. The increase was confirmed at the protein level by Western Blot analysis. The kinase activity associated with the $p185^{HER2}$ molecule indicated that the receptor was functional in all cell populations tested. The phosphorylation status of the protein, estimated by western blot with anti-phosphotyrosine antibody of anti-$p185^{HER2}$ immunoprecipitates, indicated that there were similar levels in clones and controls.

The effect of pRb2/p130 ectopic expression on SKOV3 cell growth was evaluated initially by colony formation assay. Results showed that pRb2/p130-transfected cells gave rise to a lower number of colonies than the mock-transfected cells. Further, the rate of growth was significantly decreased in comparison to that of the mock control cells ($p<0.001$), with decreases ranging from 30% to 54%. The soft agar colony formation assay indicated a significant cloning formation inhibition for each pRb2/p130 transfectant tested compared with that of mock-transfected cells ($p<0.001$). The number of foci originating from the clones decreased from 84% to 94% in comparison to mock-transfected cells.

In vivo injection of the transfected cells led to inhibition of tumorigenicity of SKOV3 cells. The tumor volume evaluated at 56 days from injection indicated a significant reduction in proliferation of the tumors originating from pRb2/p130 transfected cells when compared with tumors originating from mock-transfected cells. This is the first demonstration that Rb2/p130 can act in vivo as a tumor suppressor gene in cell lines known to be associated with expression of c-erbB-2.

Considered together, these data are clear demonstration of the ability of pRb2/p130 to inhibit cell growth by mechanisms involving specific effects on c-erbB-2 gene products. pRb2/p130 is believed to act as an oncosuppressor molecule in cells over expressing c-erbB-2. Thus, expression of pRb2/p130 provides a method for suppressing tumorigenesis induced by c-erbB-2 in a variety of human cancers including but not limited to human glioblastoma, melanoma, breast, lung, endometrial, and stomach carcinomas.

Studies with Lung Tumor Cells

The effects of pRb2/p130 on growth of tumor cells not deficient in pRb2/p130 or not known to be induced by c-erb-2, i.e., a tumor cell line containing a mutated Rb2/p130 gene, were also examined. In experiments with aggressive human lung carcinoma cell lines (H23 and A549), a murine leukemia-based (MLV-based) retroviral vector system was used for efficient delivery of the wild type Rb2/p130 gene. The H23 cell line has a mutant Rb2/p130 locus while A549 has a wild-type locus. Cells were transduced with empty virus (mock) or retroviruses carrying the puromycin resistance gene alone (MSCVPac) or in combination with pRb2/p130 (MSCVPac pRb2/p130) and selected for puromycin for 10 days. The cells transduced with the retroviruses transferring Rb2/p130 were severely growth suppressed in both the H23 and A549 cell lines. The cells were also transduced with a serial dilution of the supernatant retroviruses. The growth suppressive effects of retroviral delivery of the Rb2/p130 gene were found to be dose dependent. These data demonstrate that the growth inhibitory effects of upregulated expression of pRb2/p130 not only include Rb2/p130-deficient tumor cells but also those with wild-type Rb2/p130. In addition, these data show that the mutant pRb2/p130 protein produced in the H23 cell line does not behave in a dominant negative manner as it is unable to inhibit the growth suppressive activity of the native protein.

To confirm that the growth suppressive properties of pRb2/p130 were due to specific up-regulation of pRb2/p130 protein levels, H23 cells were transduced with empty retroviral vector or retroviruses carrying the Rb2/p130 gene. Transduction with viruses carrying the Rb2/p130 cDNA led to a significant increase in pRb2/p130 protein levels. Similar results were found with the A549 cell line that contained the wild-type pRb2/p130 protein.

The neoplastic properties of the H23 cell line following transduction with the retrovirus MSCVPac, either alone or in combination with pRb2/p130, were assessed by the ability to form colonies in soft agar. H23 cells were transduced and selected for 15 days in puromycin than seeded in duplicates into 0.3% agarose with puromycin. After 3 weeks, colonies larger than 50 cells were scored. The colony forming potential of H23 cells was significantly decreased in cells containing the Rb2/p130 transgene as compared to pooled clones transduced with MSCVPac alone. The size of the colonies was decreased by 5- to 6-fold; Rb2/p130 colonies were 82% smaller than Pac colonies. The decrease in colony number with transduction of the tumor suppressor gene was 10-fold, or 90.4%.

The effects of retroviral delivery of pRb2/p130 on tumor formation both ex vivo and in vivo were examined in nude mice. H23 tumor cells were transduced in culture with retroviruses carrying only the Pac resistance gene, or Pac and the Rb2/p130 cDNA, and selected for 15 days. Equal numbers of MSCVPac and MSCVPac-Rb2/p130 transduced cells were injected into the flank of nude mice. Transduction with MSCVPac-Rb2/p130 greatly suppressed the ability of the cells to form tumors as compared to animals injected with MSCVPac-transduced cells. There was approximately a 20-fold (99.5%) reduction in tumor-forming potential (based on average tumor weight of excised tumors) Similar results were seen when the study was repeated. For in vivo transduction of the gene, nude mice were injected with $2.5 \times 10^6$ H23 cells and tumors were allowed to grow for 15 days. After 15 days the tumors were transduced with retroviruses carrying either MSCVPac alone or MSCVPac-Rb2/p130, or the bacterial beta-galactosidase (LacZ) gene. Transduction with LacZ did not affect tumor growth rate or tumor-forming potential as compared to animals injected with MSCVPac alone. However, treatment with MSCVPac-Rb2/p130 suppressed tumor forming potential of the H23 cells as compared to that of either LacZ or MSCVPac treatment groups. The reduction in tumor growth with MSCVPac-Rb2/p130 transduction was more than 12-fold (92%). In fact, the tumors transduced with Rb2/p130 retrovirus diminished in size after a single injection, and 4 of 6 tumors completely regressed. The volume of tumors transduced with Rb2/p130 retrovirus was 4.6-fold less (79% decrease) as compared to the other treatments. Examination of the tumors formed in animals treated with the retroviral vectors were typical of lung adenocarcinoma and more than 75% of the tumor cells were highly positive for pRb2/p130 expression by immunohistochemistry of tumors transduced with the MSCVPac-Rb2/p130 vector. The suppression of tumor formation and progression in both ex vivo and in vivo transduction studies was dependent on induction of pRb2/p130 expression in the tumor cells as demonstrated through Western blot analysis of tumor cell lysates. These in vivo and ex vivo data confirm the results of the in vitro studies and show that expression of Rb2/p130 gene in tumor cells leads to an inhibition of tumor cell growth and suppression of tumor formation in animals, even in tumor cells that are not deficient in pRb2/p130.

Studies in Brain Tumor Cells

Experiments were also performed to examine the role of the pRb2/p130 gene in brain tumor growth. A modified tetracycline-regulated method was used to create an autoregulatory inducible Rb2/p130 gene expression system in the HJC-15c cell line, one of five clonal cell lines originating from a human polyomavirus-induced hamster brain tumor (Shockett, P. et al. 1995. *Proc. Natl. Acad. Sci. USA* 92:6522–6526). This cell line was chosen because it exhibited the lowest expression of Rb2/p130 mRNA and the shortest doubling time of the five clones (HJC-15a, b, c, d, and e). The parental cell line was used to create the control cell line HJCΔ5 which contains the tetracycline transactivator (tTA) under the control of the Tetp promoter. HJCΔ5 cells were used to form the HJC12 cell line which contains, in addition to tTA, the full length cDNA of the human Rb2/p130 gene downstream of the Tetp promoter. In this system, expression of Rb2/p130 is repressed in the presence of the antibiotic tetracycline and induced in its absence. Results showed that expression of Rb2/p130 is enhanced at the mRNA level and 160 fold at the protein level upon withdrawal of tetracycline from the medium. Cytochemistry determined that expression of Rb2/p130 remained in the nucleus upon induction with tetracycline.

Equal numbers of HJC12 cells were then plated in medium containing or lacking tetracycline and were grown for 15 days. Induction of pRb2/p130 resulted in a dramatic growth arrest of the cells as evidenced by colony assay. HJC12 and HJCΔ5 cells were each plated in the presence or absence of tetracycline for 24 hours then harvested. Their cell cycle profile was examined by flow cytometry which showed that upon induction of pRb2/p130 expression, nearly 90% of cells were found in the $G_0/G_1$ stage corresponding to a mean increase of 41.6% in the $G_0/G_1$ population. These results are in agreement with data from transient transfection experiments in other human cell lines wherein it was demonstrated that the growth suppressive action of pRb2/p130 is specific to the $G_0/G_1$ phase of the cell cycle (Claudio, P. P. et al. 1996. *Cancer Res.* 56:2003–2008). This effect was specific for pRb2/p130 expression since withdrawal of tetracycline from the HJCΔ5 parental cell line did not affect their cell cycle distribution.

Experiments were then performed to determine if JCV TAg, like its SV40 counterpart, interacted with pRb2/p130.

It was first confirmed that the cells line HJCΔ5 and HJC12 were transformed by JCV and not cross-contaminated with SV40 TAg. Immunoprecipitation of HJC cell lines Δ5 and 12 grown in the presence and absence of tetracycline with anti-pRb2/p130 immune serum followed by Western blotting analysis with PAB 416 detected a physical interaction between pRb2/p130 and JCV TAg.

Combined immunoprecipitation/Western blot analysis using PAB 416/anti-pRb2/p130, respectively, also detected this complex. This association increased upon induction of pRb2/p130 expression in HJC12 cells grown without tetracycline.

Since the function of pRb2/p130 is believed to be modulated through phosphorylation, the phosphorylation status in the JCV TAg complex was examined. The proteins in the HJC12 cells grown in the absence and presence of tetracycline were labeled with $^{32}P$ orthophosphate; immunoprecipitated with normal rabbit serum, pRb2/p130 immune serum, or PAB 416; and then run on a 8% SDS-polyacrylamide gel. Anti-pRb2/p130 precipitated pRb2/p130 with only the hyperphosphorylated form being visualized and 92 kDa phosphorylated form of JCV TAg. PAB 416 immunoprecipitated both the 88 and 92 kDa phosphoforms of JCV TAg but failed to precipitate pRb2/p130. Thus, the 92 kDa form of JCV TAg associates with hypophosphorylated pRb2/p130, but fails to bind hyperphosphorylated pRb2/p130. This association was detected in the HJC12 cells in both the uninduced and induced states, as well as in the HJCΔ5 cells, demonstrating that this association is specific and not merely due to inordinately high levels of pRb2/p130 protein and that neither tetracycline nor the tetracycline transactivator (tTA) affect complex formation.

The ability of induction of pRb2/p130 to overcome JCV TAg-mediated transformation and tumor formation in vivo was then examined. Nude mice were injected with either HJCΔ5 or HJC12 cells (5×10$^6$ cells) in each flank and then administered a solution of 1 mg/kg of active tetracycline hydrochloride and 1% sucrose with tetracycline or 1% sucrose without tetracycline in their drinking water. The study was performed twice. The induction of pRb2/p130 expression in the mice injected with HJC12 without tetracycline greatly retarded the rate of tumor growth as compared to mice injected with HJC12 with tetracycline. No statistically significant difference was found between the HJCΔ5 groups (with and without tetracycline) There was at least some growth of the cells in each of the mice demonstrating that the cells injected were viable and that the growth inhibitory effects were not due to nonviability of the cells prior to or during the injection process. At the end of two replicate experiments, the combined weights of the excised tumors from each of the HJC12 groups were compared. No significant difference was found in tumor weights of HJCΔ5 groups between the two experiments. HJCΔ5 tumors grew faster than HJC12 tumors and those mice had to be sacrificed before the HJC12 mice. All HJC12 mice were sacrificed at the same time in each study. In the first study, induction of pRb2/p130 expression retarded tumor growth by 2.9-fold or 66%. In the second study induction of pRb2/p130 expression inhibited tumor growth by 3.4-fold or 71%. The average effect of pRb2/p130 induction in the two replicate experiments was 3.2-fold or 69%, a statistically significant effect on tumor growth as compared to the control groups. A third experiment was performed where tetracycline was administered through subcutaneous implantation of a 42 mg, 60 day, time-release pellet designed to deliver 0.7 mg tetracycline or placebo per day. Results were similar, with significant differences in tumor growth evident upon induction of pRb2/p130 expression in HJC12 cells (a 4.3-fold inhibition or 77% inhibition of tumor growth). Western blot analysis confirmed that the tumor growth was dependent upon an increase in pRb2/p130 expression in vivo by examining protein extracts of the tumor specimens. The expression of pRb2/p130 and JCV TAg both remained nuclear upon induction of pRb2/p130 as confirmed by cytochemistry. Induction of pRb2/p130 expression and co-localization within the nuclei of the protein with JCV TAg in vivo was also demonstrated by immunohistochemistry of parallel tumor sections and cytochemistry.

These data show that the inducible system of pRb2/p130 expression functions both in vitro and in vivo to inhibit tumor cell growth in a human brain tumor cell line. These results are consistent with the studies in lung tumor cell lines and ovarian tumor cell lines.

Studies on Screening Cancer Cells

Experiments were performed to examine the application of methods of the present invention in identifying tumor cell types. In the first studies, the relationship between pRb2/p130 expression and endometrial cancer was examined. In 100 patients that had not received treatment prior to surgery, it was found that low levels of expression of this gene were associated with poor clinical prognosis. Further, tumors of these patients behaved more aggressively. The risk of dying of disease was five times greater in patients whose tumors were pRb2/p130 negative.

Screening of a panel of human tumor cells and primary Burkitt's lymphoma and nasopharyngeal tumors resulted in identification of a common site of mutation in the Rb2/p130 gene which results in nuclear exclusion of this protein. The expression of Rb2/p130 by immunocytochemistry and western blot analysis was determined in four osteosarcoma and in four lymphoid tumor cell lines using the polyclonal anti-Rb2/p130 antibody, ADLI. Cytoplasmic localization of Rb2/p130 was found in all lymphoid tumor cell lines, while all osteosarcoma cell lines showed an exclusive nuclear localization. Western blot analysis on nuclear and cytoplasmic fractions of all samples showed no substantial alteration in the molecular weight of the protein and confirmed the exclusive cytoplasmic or nuclear localization in the two types of neoplastic cell lines.

Accordingly, dependence of intracellular distribution of the protein upon mutations which differently affect the nuclear localization signal (NLS) motifs was verified. In these experiments, the structure of exons 19 through 22 of the Rb2/p130 gene which encode for the B domain and the C terminus of the protein were studied. Genomic DNA sequences from coding exons 19 through 22 were amplified and screened for mutation by SSCP analysis.

Both the direct PCR products and the DNA obtained from cutting the bands with altered migration patterns from SSCP gels were sequenced in order to identify the actual mutations. Evaluations of the sequencing chromatograms and the SSCP gels were used to determine whether or not mutations were heterozygous or homozygous. CCRF-CEM and Jurkat cell lines showed insertions in exon 22, where the NLS is located, causing a frameshift that resulted in the loss of the NLS. The Daudi cell line showed an insertion in exon 22 that occurred downstream from the putative NLS however, an insertion in exon 21 of Daudi cells effectively causes the loss of the NLS present in exon 22 by the resulting shift in the coding frame. Similarly, no mutations or insertions were observed in exon 22 of the Molt-4 cell line; however, an insertion in exon 21 gave a frameshift causing the loss of the bipartite NLS located in exon 22. In contrast, all osteosarcoma cell lines exhibited only point mutations in exons 19, 20 and 21 which did not alter the NLS.

The functional consequences of disruptions in the NLS of pRb2/p130 were then determined. Experiments were first performed to determine whether or not this region can serve in and of itself as a NLS. The NLS of pRb2/p130 from amino acids 1082 to 1102 was fused to the amino-terminus of EGFP in the pEGFP-N1 [pEGFP-N1-NLS] expression vector which expresses a human codon-optimized, red-shifted green fluorescent protein that can be fused to heterologous proteins serving as a fluorescent tag (Clontech Laboratories, Inc., Palo Alto, Calif.). EGFP is a low molecular weight protein that lacks any localization signal and is equally distributed in the nuclear and cytoplasmic compartments. Point mutations were also constructed in the first region of the bipartite NLS resulting in a change in amino acids K-1082 to N and R-1083 to Q [pEGFP-N1-NLS-NQ1], in the second site K-1100 to N and R-1102 to Q [pEGFP-N1-NLA-NQ2], as well as the combination of mutations in both bipartite sites [pEGFP-N1-NLS-NQ1&2]. The plasmids were transfected into Saos-2 cells, and the locations of the ectopically expressed proteins were determined by fluorescence microscopy. Saos-2 cells were chosen because Rb2/p130 is found to be exclusively nuclear in the cells confirming that they do not harbor any mutations in other proteins which may affect nuclear shuttling directed by this regions. The cells were counterstained with propidium iodide. In pEGFP-N1 transfected cells, EGFP was expressed ubiquitously in the cell. Fusion of the wild-type bipartite NLS to EGFP localized expression exclusively in the nucleus. EGFP fused to point mutations in either the upstream region or downstream region of the bipartite NLS resulted in mostly nuclear expression. Mutation in both bipartite sites resulted in an expression pattern without any nuclear targeting wherein the fusion protein equilibrated between the nuclear and cytoplasmic compartments in similar fashion to cells transfected with pEGFP-N1. Accordingly, this region of pRb2/p130 serves as a bipartite NLS where both the upstream and the downstream signals can independently dictate nuclear expression. Only combined mutations in both the bipartite sites resulted in complete loss of exclusive nuclear expression.

The effects of mutations on the growth suppressive function of pRb2/p130 were then analyzed by recreating the NQ point mutation in PCR based site-directed mutagenesis in the full length pRb2/p130 protein in the pcDNA3 mammalian expression vector that drives expression by the constitutive cytomegalovirus (CMV) promoter. Each of the constructs was tagged at the carboxy-terminus with a single HA-epitope (hemagglutinin tag from *Hemophilus influenzae*) so that exogenous expression could be distinguished from that of the endogenous protein. Each of the mutants and the wild-type plasmids were expressed at approximately the same level as determined by immunoprecipitation and western blot analysis with the HA-epitope. Saos-2 cells were transfected with the mutant plasmids as well as vector alone and plasmids expressing the wild-type pRb2/p130 protein as controls, and their affects on cellular proliferation were measured by flow cytometry analysis. Mutations within either the upstream or downstream regions of the bipartite NLS had no significant effect on the growth suppressive activity of pRb2/p130. Their expression still led to $G_0/G_1$ phase growth arrest which was consistent with the localization data demonstrating that each of the bipartite signals can independently direct nuclear transport. The growth suppressive activity of the combined mutations in both bipartite sites was annihilated. Cells expressing this construct were clearly cycling. Addition of the c-myc major NLS to the carboxy terminus of these mutants by targeting their expression to the nucleus restored their $G_0/G_1$ growth arresting activity to that of the wild-type protein. This demonstrated that the reduced biological activity of pRb2/p130 conferred by these mutations was indeed by their disruption of the nuclear localization of pRb2/p130 and not by induction of gross conformational changes and/or the abrogation of binding to critical protein targets. Additionally, the growth suppressive effects of pRb2/p130 overexpression were not due to mere toxicity of the protein since point mutation in the protein effectively abrogated this activity. Furthermore, pRb2/p130 must be in the nucleus to regulate $G_1$ progression. The same genetic analysis was also performed on primary Burkitt's lymphoma and primary nasopharyngeal carcinomas, positive for Epstein-Barr virus (EBV). The two primary nasopharyngeal carcinomas displayed two heterologous point mutations in exon 20 which are also present in the human nasopharyngeal cell line, HONE-1. Moreover, insertions in exon 22 of the primary nasopharyngeal carcinoma and of HONE-1 were also found, which cause a frameshift with consequential loss of the nuclear localization signal. The point mutations and insertion present in two primary Burkitt's lymphomas and in the two primary nasopharyngeal carcinomas are the same as those found in Daudi and HONE-1 cell lines, respectively.

Screening studies were also performed in several human lung carcinoma cell lines (H23, A549, H69, H82, and U1752) to determine if lack of Rb2/p130 protein observed in some tumor types correlated to a genetic mutation. Specifically, lung tumor cells were screened for mutations in exons 19 and 20 (B domain) as well as exons 21 and 22 (carboxy terminus) of the Rb2/p130 gene. Mutations were detected by SSCP analysis and confirmed by sequencing in 4 of 5 cell lines screened (H23, H69, H82, and U1752); A549 was found to be wild-type for the exons examined (no mutations). The same point mutations in exon 20 were found in 3 cell lines, corresponding to a coding region of the B domain. The substitution of an A for a G at nucleotide 3069 is a silent mutation; however, the same substitution at nucleotide 3074 changes Arg to Lys within a critical position in the bipartite nuclear localization signal of pRb2/p130. Both transitions were found in H69, H82 and U1752 small cell lung carcinoma lines. Thus, this region of the gene appears to be a mutational hot spot, the identification of which may be useful in developing a rapid diagnostic mutational screening assay.

In the H23 adenocarcinoma cell line, 5 point mutations, all G to A transitions, which altered 5 amino acids, were found in close proximity within exon 21 at nucleotides 3191, 3209, 3278, 3280, and 3285. Three polar basic Arg amino acids with their reactive guanidine groups were substituted with Lys (aa 1040) and Gln (aa 1047 and aa 1070). The alteration of a basic amino acid to a neutral amide-containing amino acid such as Gln, as well as the loss of the guanidine group, may have significant effects on the secondary and tertiary structure of the protein, as well as affecting protein interactions. Additionally, the substitution of a polar amino acid with a hydroxyl group such as Ser for the nonpolar aromatic Phe (aa 1074) may also significantly affect protein folding and functional interactions.

Primary patient samples of lung carcinoma were also screened for mutations in exon 19 through 22 of the Rb2/p130 gene. The Rb2/p130 gene was found to be mutated in exon 21 and/or 22 in 12 of 14 tumors analyzed. Insertion of an A in exon 22 causing a frameshift in either codon 11 and/or 1084 was found in 4 of 12 samples. This frameshift disrupts the bipartite nuclear localization of pRb2/p130 necessary for the exclusive nuclear expression of pRb2/p130 which is essential for the $G_0/G_1$ growth inhibitory function of pRb2/p130. A point mutation in codon 1083, which is within the upstream region of the bipartite nuclear localization and changes a critical Asn residue to either Phe or Thr was identified in 7 of the 12 mutated samples.

Thus, mutations disrupting the nuclear expression of pRb2/p130 appear to be a common mechanism of functional inactivation of this growth regulatory protein in primary tissues. Similar mutants in Rb/p105 have been shown to display reduced growth inhibition in vitro, probably due to insufficient levels of the protein in the nucleus (Zacksenhaus et al. Mol. Cell Biol. 1993 13:4588–4599). A similar phenomena occurs in the Rb2/p130 cytoplasmic mutants and is believed to predispose the cells to neoplastic transformation and/or give the cells a more aggressive or enhanced malignant phenotype. This is supported by immunohistochemical studies where the grade of the tumor inversely correlates with the expression level of pRb2/p130 (Baldi et al. Clinical Cancer Res. 1996 7:1239–1245). Accordingly, screening tumor cells to detect for mutations resulting in the loss of the NLS of Rb2/p130 serves as a means for determining the aggressive and malignant phenotype of the tumor. Further, screening of tumors to identify those with mutations in this gene is useful in identifying those tumors treatable by administration of Rb2/p130. By "treatable" it is meant that administration of Rb2/p130 will inhibit the growth of this tumor.

Accordingly, the present invention provides methods for identifying aggressive and malignant tumors to be treated with a plasmid or vector comprising pRb2/p120 and methods for reversing the tumorigenicity by transfecting tumor cells with a plasmid or vector comprising pRb2/p130. In a preferred embodiment, Rb2/p130 cDNA is subcloned into an appropriate viral vector in accordance with methods of plasmid construction well known in the art and described for example by Claudio et al. (1994 Cancer Res. 54:5556–5560). As will be obvious to those of skill in the art upon this disclosure, however, appropriate vectors other than those described by Claudio et al. (1994) could be routinely selected. Selection of an appropriate vector is based upon adequate expression of the gene with minimal viral gene expression. One preferred embodiment of a vector useful in the present invention is the pAd.CMV-Link.1 adenoviral vector. Alternatively, using a transient three-plasmid expression system (plasmids encoding env, gag-pol, and Rb2/p130), the full length pRb2/p130 gene can be cloned into retroviral vectors. In another embodiment using plasmid pTet-tTak containing the gene for tetracycline trans-activator under the control of the Tetp promoter, the full-length cDNA of human Rb2/p130 gene can be subcloned downstream of the Tetp promoter into the HindIII site of the UHD hyg BH plasmid. Yet another embodiment would involve using the MSCVPac plasmid where the full length cDNA sequence of Rb2/p130 was subcloned into the retroviral vector.

The vector encoding pRb2/p130 is then transfected into tumor cells. This can be accomplished using methods known to those of skill in the art. In a preferred embodiment, the viral vectors are administered to a mammal, preferably a human. In one embodiment, the vector containing the pRb2/p130 gene is administered to suppress growth of tumor cells and prevent tumor progression and metastasis through expression of the tumor suppressor gene. In this embodiment, the method of transfection will vary depending on the patient population under consideration. For example, in patients with operable tumors, the tumor area can be coated with the viral vector following resection by the surgeon to limit recurrence. Alternatively, the tumor mass can be injected with the vector prior to surgery. In patients with inoperable tumor masses, the patient can receive injections of the vector directly into the tumor mass if accessible, or it can be selectively injected intra-arterially to arteries directly feeding the tumor mass or inaccessible tumor (Claudio et al. 1990 Cancer 65:1465–1471; Claudio et al. 1992 Reg. Cancer. Treat. 4:180–187). Lung tumors can treated by inhalation of the vector.

It is preferred that the vectors be administered in a pharmaceutically acceptable carrier for injection such as a sterile aqueous solution or dispersion. Dose and duration of treatment is determined individually depending on the degree and rate of improvement. Such determinations are performed routinely by those of skill in the art.

The following nonlimiting examples are provided to further illustrate the present invention.

EXAMPLES

Example 1

Use of pRb2/p130 in Ovarian Cancer

Cloning the Rb2/p130 cDNA

The full length of the pRb2/p130 gene was subcloned into the pAd.CMV-Link.1 adenoviral vector. This was accomplished by restricting the sense construct of the pcDNA3:Rb2/p130 with HindIII and SalI. The SalI cut the vector backbone to make it easier to isolate the full length rB2/p130 cDNA with HindIII sites at the 5' and 3' ends. The pAd CMV-Link1 vector was restricted with HindIII in its multiple cloning site and was ligated to the Rb2/p130 insert cDNA to form both pAd.CMV-Link.1:Rb2/p130 sense and antisense constructs. This pcDNA3:Rb2/p130 sense vector was described by Claudio et al. (1994).

The full length cDNA sequence of Rb2/p130 was also subcloned into the retroviral vectors MSCVneoEB and MSCVpac, both in the sense and antisense orientations. To accomplish this, the pcDNA3 pRb2/p130 sense, cloned BamHI-NotI was cut with NotI and religated with a linker oligonucleotide that changed the NotI site to a BamHI site (5' GGCCGGGGGATCCCCC 3' (SEQ ID NO: 1)). The pRb2/p130 fragment with BamHI sites and the 5' and 3' sites was purified and subcloned into MSCVneoEB and MSCVpac cut with Bgl 11 either in the sense or in the antisense orientation.

Transfection of Cells

Cells targeted for transfection with the pRb2/p130 plasmid were selected and cultured. Transfection of cell lines was by standard calcium-phosphate precipitation methods (Hutner et al. 1981 J. Cell. Biol. 91:153–156). DNA precipitates were left on cells for 12 hours. Cells were then washed with phosphate-buffered saline (PBS) and cultured in fresh media.

Suppression of Tumorigenicity in Vitro

Human ovarian carcinoma cell line SKOV3 was purchased from the American Type Culture Collection and maintained at 37° C. in a humidified atmosphere of 5% $CO_2$ in air, cultured in RPMI-1640 medium (Sigma Chemical Co.) Supplemented with 10% heat-inactivated FCS (Hyclone, Logan, Utah) and 2 mM L-glutamine. In transfected cells medium 300 μg/ml G-418 (genectin) was added.

The plasmids pcDNA3 pRb2/p130 sense and the empty vector pcDNA3 were used. They were prepared as described by Claudio et al. (1994 *Cancer Res.* 54:5556–5560). SKOV3 cells at 80% confluence in serum-free medium were transfected with 50 μg of Lipofectin plus 20 μg of plasmid. Transfectants were left overnight at 37° C. and, after addition of complete medium, maintained in culture for an additional 48 hours. The cells were then trypsinized and plated in the presence of 500 μg/ml of G-418. Individual growing colonies were picked and expanded and maintained in the presence of 300 μg/ml of G-418.

To demonstrate colony formation ability, the transfected cells were plated, $10_6$ cells per dish, in duplicate and after 3 weeks were stained for 15 minutes in TB methylene blue and photographed (medium contained 500 μg/ml of G-418). Growth rate in vitro was examined by plating cells in 96-well culture plates in 0.2 ml of culture medium. At different times of culture, 5 mg/ml of 3-(4,5-dimethylthiazol-2-yl)-2,5-diphenyltetrazolium bromide in phosphate buffered saline was added. After 4 hours incubation, the medium was removed, and the crystals were dissolved in 2-propanol and the supernatant spectrophotometrically evaluated at a wavelength of 570 nm (described by Alley et al. 1988 *Cancer Res.* 48:589–601). Soft agar colony formation was demonstrated by plating cells in 6 well plates in semisolid medium containing 0.35% Bacto Agar (Difco Laboratories) supplemented with 30% FCS and 300 μg/ml G-418, over a 0.7% agarose layer. Colonies were scored after 27 days of incubation at 37° C. in 5% $CO_2$ in air.

Northern blot analysis was used to demonstrate an increase in pRb2/p130 mRNA levels in transfected clones as compared with mock and wild-type SKOV3 cells. Briefly, the assay involved extraction of RNA by RNAzol B RNA isolation solvent (TEL-TEST, INC.) Following the supplier's instructions. RNA was then electrophoresed in 1% agarose-formaldehyde gel, transferred onto nitrocellulose filter and immobilized by UV -crosslinking. Hybridization was carried out using a ($^{32}$p)dCTP (Amersham) probe, obtained by BamHI and Xbal digestion of pRb2/p130 cDNA corresponding to the 5' end (nucleotides 1–1032), using random-primed DNA labeling kit (Boehringer Mannheim Biochemicals). After stripping, membrane was hybridized with a control ($^{32}$p)dCTO beta-actin probe (see Gunning et al. 1983 *Mo. Cell. Biol.* 3:787–795).

Increases in mRNA was confirmed at the protein level by Western blot analysis. Briefly, cells were trypsinized, washed twice with cold PBS and solubilized for 50 minutes on ice in lysis buffer (50 mM Tris-HCl at pH 7.4, 5 mM EDTA, 250 mM NaCl, 50 mM NaF, 1% Nonidet P40, 10 μg/ml leupeptin, 1 mM PMSF, 1 mM $Na_3VO_4$ and 1 μM Okadaic acid). Cell lysates were cleared by centrifugation at 4° C. for 10 minutes at 10,000 ×g. Protein concentration was determined by the BCA protein assay reagent (Pierce Biochemical Company). After heating at 95° C. for 5 minutes, for each sample 100 μg of total protein was electrophoresed in a 7.5% and 10% SDS-PAGE under non-reducing conditions. Separated proteins were then electrophoresed to Hybond-C paper (Amersham) and incubated at room temperature for 1 to 2 hours with the primary antibody followed by incubation with $^{125}$I-goat anti-mouse 7S immunoglobulin (Amersham) and autoradiography; or by anti-rabbit immunoglobulin and/or anti mouse immunoglobulin horseradish peroxidase-linked whole antibodies (1:10000; Amersham) and visualized using the ECL detection system (Amersham).

Monoclonal antibodies (Mabs) used included: anti-p185$^{HER2}$MGR2 (10 μg/ml) previously described (Tagliabue et al. 1991 *Int. J. Cancer* 47:933–937), and Ab3 (2 μg/ml; Oncogene Science) , and anti-phosphotyrosine 4G10 (4 μg/ml; Upstate Biotechnology Inc.). The polyclonal anti-pRb2/p130 serum (1:500) previously described was used (Baldi et al. 1995 *J. Cell. Biochem.* 59:402–408).

Functional activity of the p185$^{HER2}$ molecule in cells was assessed by examining in vitro kinase activity. Briefly, cell lysates (2 mg protein/sample)obtained as described above were immunoprecipitated after preclearing for 30 minutes with GammaBind Plus Sepharose (Pharmacia Biotech) by incubation on a rocker for 1 hour at 4° C. with specific antibodies or rabbit or mouse normal sera as negative controls. Twenty μl of sepharose was added, and after 1 hour incubation, immune complexes were separated by centrifugation, washed three times with lysis buffer and once in Kinase buffer (20 mM Hepes, 10 mM magnesium acetate, 1 mM dithiothreitol, 20 μM ATP). In vitro kinase assay was performed as described in Giordano et al. *Science* 1991 253:1271–1275.

Suppression of Tumorigenicity in vivo

Six week old athymic mice were purchased from Charles River. Cells from the SKOV3 lines (discussed in detail above) that had been transfected with pRb2/p130. were trypsinized, washed twice with cold PBS and counted. Then, $4 \times 10^6$ cells were injected subcutaneously into the right flank of mice under aseptic conditions. Tumor growth was measured twice each week and the tumor volume calculated using the following formula: $0.5 \times d_1^2 \times d_2$, where $d_1$ is the smaller and $d_2$ the larger diameter of the tumor.

Example 2

Use of pRb2/p130 in Lung Cancer

Cloning the pRb2/p130 cDNA

The Lull length CDNA sequence of Rb2/p130 was subcloned into the retroviral vectors MSCVneoEB ad MSCV-Pac both in the sense and antisense orientations. Briefly, the pcDNA3 pRb2/p130 sense, cloned BamHl-Not 1 was cut with Not 1 and religated with an oligo that changed the Not 1 site to a BamHl site (5' GGCCGGGGGATCCCCC 3' (SEQ ID NO: 1)). The pRb2/p130 fragment BamHl-BamHl was purified and subcloned into MSCVneoEB and MSCV-Pac cut with Bgl II either in the sense or in the antisense orientation.

Transfection of Cells

Transient DNA cotransfections were performed on 293T/17 cells by calcium phosphate precipitation. The retroviral supernatant was collected 48 hours post-transfection, filtered through 0.45 μm filters and titered by transducing H23 and A549 cell lines. Viral titers were determined by counting the FITC positive cells following PRINS labeling.

For the PRINS reaction, cells were plated on slides at a concentration of $5 \times 10^5$ cells/dish. Then the cells were infected with either 20 μl, 50 μl, 100 μor 1 ml of retroviruses carrying the puromycin gene resistance alone or in combination with the Rb2/p130 cDNA in either the sense or antisense orientation. As a negative control, cells were transduced with supernatant collected from a cotransfection of 293T/17 cells with only the plasmids carrying gag/pol and env (empty virus). Samples were fixed in methanol and glacial acetic acid 3:1 for 10 minutes at room temperature and air dried for 12–24 hours. The next day, the samples were dehydrated in a series of ethanol solutions for 5 minutes each (70%-80%-100%) and air dried.

For the PRINS reaction, the primers PUR 3 (5'-GTCCTTCGGGCACCTC-3'; SEQ ID NO: 2) and PUR 5 (TCACCGAGCTGCAAGAAC-3'; SEQ ID NO:3) were used to amplify a stretch of 425 bp in the puromycin resistance gene present in the plasmids MSCVPac and MSCVPac-pRb2/p130, sense and antisense as well. Each sample was incubated with 50 μl of the reactions mix at 95° C. for 5 minutes, at 58° C. for 30 minutes, and at 74° C. for 90 minutes. The reaction mix contained the following: 100 ng of each primer, 1×PCR buffer containing 15 mM $MgCl_2$, a mix of dNTP containing 1 mM DATP, 1 mM dCTP, 1 mM dGTP, 0.65 mM dTTP, 0.35 mM DIG-11-dUTP, alkali-labile and 2.5 U of Taq DNA polymerase. The reaction mix was deposited on each slide and a cover slide was placed on top and sealed with rubber cement glue. After elongation at 74° C., the slides were washed twice in 2×SSC and 2% BSA for 10 minutes at room temperature. Anti-digoxigenin-FITC conjugated antibody was diluted 1:200 into 2×SSC and 2% BSA and used for detection of DIG-11-dUTP incorporation. The slides were incubated with the antibody for minutes at room temperature in a dark humid chamber and then washed twice in 2×SSC for 5 minutes to remove excess antibody.

The samples were also treated with a solution of 1 μg/ml of propidium iodide to stain the unlabeled DNA and then washed in water. Slides were then observed and positive cells were counted and photographed under a confocal microscope. The same process was applied to frozen tumor sections from H23 tumors grown in nude mice.

Suppression of Tumorigenicity in vitro

Soft-agar colony formation assays were performed as described by Huang, H-J. et al. 1988. Science 242:1563–1566. H23 cells were plated at a density of $1\times10^6$ cells/dish in a 10 cm culture dish the day before infection. Cells were infected overnight at 37° C. with 1 ml of retroviruses carrying puromycin resistance alone or in combination with the Rb2/p130 cDNA. Cells were selected in medium containing 2 μg/ml of puromycin for 15 days. Equal numbers of cells ($5\times10^3$) for each infection were seeded in duplicate in 0.3% agar containing 2 μg/ml of puromycin in 60 mm/6 well culture dishes. After 20 days of incubation at 37° C, colonies containing at least 50 cells were counted, and the value for each of the duplicate plates was averaged.

Suppression of Tumorigenicity in vivo

Tumors were subcutaneously generated in nude mice (female NU/NU-nuBR outbred, isolator maintained mice, 4–5 weeks old from Charles River) by the injection of H23 cells. For ex vivo studies, H23 tumor cells were transduced in culture with $1\times10^7$ retroviruses/10 cm dish carrying only the Pac resistance gene or additionally the Rb2/p130 cDNA and selected for 15 days. Equal numbers of Pac and Rb2/p130 transduced cells ($2.5\times10^6$) were then injected into each dorsal flank of nude mice and grown for about 4 weeks, or until the control Pac retrovirus tumors reached an area of approximately 1 $cm^2$. This study was repeated under exactly the same conditions. For the in vivo transduction studies, nude mice were injected along their dorsal flanks with $2.5\times10^6$ H23 cells. After 15 days the tumors were transduced with $5\times10^6$ retroviruses carrying the Pac resistance gene alone or additionally the beta-galactosidase (LacZ) gene as a control or the Rb2/p130 cDNA. The animals were sacrificed when Pac or LacZ retroviral transduced tumors reached a size of approximately 1 $cm^2$ (approximately 3 weeks). Animal weight was monitored weekly. Tumor growth was followed by measuring with a caliper the longest axis of the tumor and the axis perpendicular to this. Tumor volume was calculated using the formula tumor volume= (length) (width)²/2. The tumors were then excised and weighed prior to processing. Tissues to be used for molecular biological analysis were snap frozen in liquid nitrogen and stored at −80° C.

Example 3

Use of pRb2/p130 in Brain Cancer

Cloning the Rb2/p130 cDNA

The plasmids used included pcDNA3 (conferring neomycin resistance) and pTet-tTak (containing the gene for tetracycline transactivator). The full length CDNA of the human Rb2/p130 gene was subcloned downstream of the Tetp promoter into the HindIII site of the UHD hyg BH plasmid as described by Gossen, M. and Bujard, H. *Proc. Natl. Acad. Sci. USA* 1992 89:5547–5551.

Transfection of Cells

The HJC-15c clonal cell line originating from a JCV-induced hamster brain tumor described by Raj, G. V. et al. 1995. *Int. J. Oncol.* 7:801–808, HJCΔ5, 293, and COS7 cells were grown in Dulbecco's Modified Eagle's Media (DMEM) supplemented with 5% fetal calf serum and antibiotics. Both HJCΔ5 and HJC12 cells were maintained in DMEM supplemented with 5% calf serum, antibiotics, and 2 μg/ml of tetracycline. All transfections were performed using the standard suspension calcium phosphate precipitation method. The HJCΔ5 cell line was formed by stable co-transfection of the HJC-15c cell line with pcDNA3 and pTet-tTak at a 1:50 ratio, respectively. The cells were selected in 1000 μg/ml of G418. Individual colonies were picked and screened by transient transfection of the UHD hyg BH-Rb2/p130 plasmid in the presence and the absence of 2 μg/ml of tetracycline in the medium. Forty-eight hours post-transfection the cells were harvested and screened by Western blot analysis with the ADL1 polyclonal antibody to Rb2/p130 to select for the clone with the best induction of pRb2/p130 expression in the absence of tetracycline. The positive clones were then grown in the absence of tetracycline for a prolonged time (4–5 weeks) to ensure that the expression of tTA was not affecting cell growth or morphology. The HJC12 clone was formed by stable transfection of the HJCΔ5 clone with the UHD hyg BH-Rb2/p130 plasmid and the cells were selected with 500 μg/ml of G418, 500 μg/ml hygromycin and 2 μg/ml of tetracycline to repress exogenous pRb2/p130 expression. The clones were grown under the constant presence of tetracycline (2 μg/ml). The clones were screened by placing the cells in medium with or without tetracycline for 48 hours and Western blotting with the ADL1 antibody for the clone with the best induction of pRb2/p130 expression in the absence of tetracycline.

Suppression of Tumorigenicity in vitro

The colony formation assays were performed in triplicate as described by Claudio, P. P. et al. 1994. *Cancer Res.* 54:5556–5560 and Claudio, P. P. et al. 1996. *Cancer Res.* 56:2003–2008. HJC12 cells were plated at $1.5\times10^5$ cells/plate in the presence or absence of tetracycline. The expression of pRb2/p130 was induced in HJC12 cells by washing the cells thoroughly with PBS and placing them in fresh medium lacking tetracycline. Expression of exogenous Rb2/p130 was repressed by the addition of 2 μg/ml tetracycline to the medium. Selective pressure was continued by maintaining the cells in 500 μg/ml G418 and 250 μg/ml hygromycin.

Suppression of Tumorigenicity in vivo

Tumors were generated subcutaneously in nude mice (female NU/NU-nuBR outbred, isolator maintained mice 4–5 weeks old from Charles River) by the injection of HJCΔ5 or HJC12 cells. Cells were grown in medium containing 2 μg/ml of tetracycline and washed prior to injection. The mice were treated with tetracycline for 4 days prior to injection. Mice were injected subcutaneously along their left and right flanks with $5 \times 10^6$ cells per flank while under anesthesia with isopropane gas. There were four groups of animals, two groups injected with HJC12 cells and treatment with tetracycline continued following injection in one of those groups, the other two groups injected with HJCΔ5 cells and again only one received tetracycline. Animal weight was monitored weekly. Tumor growth and tumor volume were monitored as described above for experiments with lung tumor cells. Tetracycline was administered to animals by adding the powder in sucrose to their drinking water. Water was changed every day. Animals were sacrificed 10 weeks after injection of the cells lines or when tumors reached a size of 1 cm$^2$. The tumors were then excised and weighed.

Example 4

Screening Cancer Cells for Mutant Rb2/p130

Cell Culture and Transfection

Nasopharyngeal carcinoma cell line HONE-1 was obtained as described by Claudio et al. *Cancer Res.* 1994 54:5556–5560.Other cell lines were obtained from American Type Culture Collection, Rockville Md. and European Collection of Animals Cell Culture, Europe. The four human osteosarcomas, Saos-2, Hos, MG-63, U20S and HONE-1 were grown at 37° C. in Dulbecco's modified Eagle's medium (DMEM) supplemented with 15% fetal bovine serum (FBS). CCRF-CEM (acute T lymphoblastic leukemia), Jurkat (leukemia T-cell lymphoblast), Molt-4 (acute T lymphoblastic leukemia) and Daudi (B lymphoblast Burkitt's lymphoma) were grown in RPMI 1640 plus 10% FBS.

Saos-2 cells were plated at a concentration of $1 \times 10^6$ cells per plate in triplicate. Following 24 hours the cells were transfected by a standard calcium phosphate precipitation method as taught by Claudio et al. *Cancer Res.* 1996 56:2003–2008.

Immunofluorescence and Confocal Microscopy Analysis

All cell lines were fixed in 4% paraformaldehyde in 1×PBS permeabilized with 0.8% Triton X-100 for 15 minutes. Slides were incubated to block non specific binding with 2% BSA, 3% normal goat serum in PBS (immunoreaction buffer) for 30 minutes at 37° C. and then reacted with primary polyclonal anti-Rb2/p130 antibody, ADLI, diluted in immunoreaction buffer 1:50 for 3 hours at 37° C. and with secondary FITC-conjugated goat anti-rabbit IgG (Sigma Chemical Co., St Louis, Mo.) for 1 hour at 37° C. DNA was counterstained with DAPI (Sigma Chemical Co.) to assess the nuclear domains. The samples were analyzed by a confocal laser scanning microscope Zeiss LSM410 (Carl Zeiss, Germany) equipped with a 100×oil emersion lens (N.A.=1.4) and a 488/514 nm argon laser. Image acquisition, recording and filtering were performed on z series of confocal data (stacks) by an Indy 4600 graphic workstation (Silicon Graphics, USA) as described by Neri et al. *J. Histochem. Cytochem.* 1997 45:295–305. Specificity of the ADLI antibody for recognizing pRb2/p130 has been demonstrated by Baldi, A. *J. Cell. Biochem.* 1995 59:402–408 and Claudio et al. *Cancer Res.* 1996 56:2003–2008.

Preparation of Cell Fractions and Western blot analysis

Whole cell lysates were prepared by resuspending pelleted cells in 200 μl of lysis buffer (50 mM Tris HCl, 5 mM EDTA, 250 mM NaCl, 50 mM NaF, 0.1% Triton, 0.1 mM Na$_3$VO$_4$, plus protease inhibitors 1 mM phenylmethylsulphonyl fluoride (PMSF), 1 μg/ml aprotinin and leupeptin).

Nuclei from osteosarcoma cells were obtained as described by Martelli et al. *Nature* 1992 358:242–244. Nuclei from peripheral blood lymphocytes or lymphoid cell lines were obtained by suspending $10 \times 10^6$ cells in 20 ml of 4° C. lysis buffer (10 mM Tris HCl at pH 7.4, 2 mM MgCl$_2$, 0.5 mM PMSF, 1 μg/ml aprotinin and leupeptin, 0.5 μg/ml soybean trypsin inhibitor) for 10 minutes in ice. After addition of Triton-X 100 to a final concentration of 0.2%, cells were sheared by 1 passage through a 22-gauge needle. Nuclear purity was first assessed by high magnification phase contrast microscopy. Nuclei from both cell groups were recovered by centrifugation at 400 g for 6 minutes. The supernatant was removed and kept as the cytoplasmic fraction. Nuclei were washed in a graded series of Tris HCl buffer containing MgCl$_2$ from 2 mM to a final concentration of 5 mM (TM5).

Nuclei were resuspended in a final volume of 300 μl TM5; 250 U of DNase (Sigma Chemical Co.) were added and were incubated for 60 minutes in ice under mild shaking. Cytoplasmic fractions were treated in similar fashion. Finally, nuclear and cytoplasmic proteins were precipitated by chloroform/methanol as described by Wessel, D. and Flugge, U. I. *Anal. Biochem.* 1984 138:141–143 and dissolved in Laemmli buffer (62.5 mM Tris HCl, pH 6.8, 2% SDS, 10% glycerol, 5% mercaptoethanol, bromophenol blue).

Western blotting on cell lysates or cell fractions was performed as described by De Luca et al. *J. Biol. Chem.* 1997 272:20971–20974. Cytoplasm and membrane-depleted nuclei were balanced to 50 μg of whole cell lysate proteins. To assess nuclear purity, whole cell lysates, cytoplasm and nuclei were analyzed with a polyclonal antibody directed against β-tubulin (Sigma Chemical Co.).

PCR and SSCP Analysis

The PCR reaction mix (50 μl) contained genomic DNA or DNA extracted from SSCP gels at the final concentration of 4 ng/μl, 0.2 mM of each of the four deoxynucleotide triphosphates and [$^{35}$S]-dATP (only in the sample used for the SSCP analysis), 2 U of Klen Taq 1 (Ab Peptides, USA) and the primer panels at the final concentration of 0.4 μM each. Thirty-five cycles of denaturation (95° C., 1 minute), annealing (55° C., 1 minute) and extension (72° C., 1 minute) linked to one cycle at 72° C. for 7 minutes were carried out in a thermal cycler (Perkin Elmer, Norwalk, Conn.). The intron-specific primers used to amplify the exons from genomic DNA are summarized in Table 1.

TABLE 1

PCR primers used to amplify genomic DNA

| Oligonucleotide localization | Sequence (5'- 3') | SEQ ID NO: | Size (bp) |
|---|---|---|---|
| Exon 19 | AGGTCCTATCACCAAGGGTGT | 4 | 250 |
| Exon 19 rev | GCTTAGTTACTTCTTCAAGGC | 5 | |
| Exon 20 | GAGAAAGTTAATATCCTAGCTG | 6 | 446 |
| Exon 20 rev | GTGAATGGTCCATATATAAATCA | 7 | |
| Exon 21 | TGGTTTAGCACACCTCTTCAC | 8 | 325 |
| Exon 21 rev | GCTTAGCACAAACCCTGTTTC | 9 | |
| Exon 22 | CTGAGCTATGTGCATTTGCA | 10 | 232 |
| Exon 22 rev | AAGGCTGCTGCTAAACAGAT | 11 | |

For SSCP analysis, MDE gel solution (FMC BioProducts, Rockland, Me.) supplied as 2×liquid concentrate was used. For 100 ml total volume: 25 ml of 2×MDE gel solution, 6 ml of 10×TBE, 69 ml deionized water, 40 µl of TEMED and 400 µl of 10% APS were used as recommended by AT Biochem. The [$^{35}$S]-labeled PCR products were heated to 94° C. for 2 minutes and placed directly on ice for several minutes. The samples were run through the MDE gel at 8 Watts constant power for 8 hours at 15° C., in 0.6×TBE running buffer.

Extracted of the Shifted Bands from the SSCP Gel

The developed film was aligned with the corresponding SSCP gel to identify the DNA band of interest. The band was cut out with a razor blade and placed in a microcentrifuge tube. RNase free distilled water (50 µl) was added to the tube and incubated 10 minutes at room temperature. The tube was boiled 15 minutes and microcentrifuged 2 minutes at high speed to pellet the gel slice and the paper debris. The supernatant was placed into a clean tube and used for PCR reaction. The PCR product was used for automated DNA sequencing.

Sequence Analysis

The PCR products were resolved on a 1.5% ethidium bromide stained agarose gel. Bands were cut from the gels. DNA was purified using QUIAquick gel extraction kit (Qiagen, Santa Clarita, Calif.) and utilized for automated DNA sequencing using the dideoxy terminator reaction chemistry for sequence analysis on the Applied Biosystem Model 373A DNA sequencer.

Site-directed In Vitro Mutagenesis

Oligonucleotides encoding the bipartite NLS of pRB2/p130, the region encoding amino acids 1082 to 1002, were synthesized with the addition of an ATG transcriptional start site at the amino-terminus, 5' HindIII and 3' BamHI restriction site, and two adenosine residues just prior to the BamHI site to keep the heterologous fusion protein between the bipartite NLS and the amino-terminus of the EGFP protein in frame. The oligonucleotides were annealed and ligated into the HindIII and BamHI restriction sites of the pEGFP-N1 expression construct to form the pEGFP-N1-NLS construct. The pEGFP-N1-NLS-NQ1, pEGFP-N1-NLS-NQ2, and the pEGFP-N1-NLS-Nq1&2 were constructed so that synthesized oligonucleotides encoded point mutations that altered amino acids K-1082 to N and R-1083 to Q in the first bipartite, K-1100 to N and R-1102 to Q in the second site, and the K to N and R to Q were combined in both sites, respectively.

The point mutations in the bipartite NLS of the full-length Rb2/p130 cDNA were formed by an extra long PCR technique described by Sang et al. *Anal. Biochem.* 1996 233:142–144 that permits site specific mutagenesis. The wild-type Rb2/p130 cDNA with an exogenous hemagglutinin epitope (HA) at the carboxy terminus (pcDNA3-Rb2/p130-HA) as well as the HA epitope and the c-myc major NLS (HAN) at the carboxy terminus (pcDNA3-Rb2/p130-HAN) in the pcDNA3 vector were used as PCR templates. The pcDNA3-Rb2/p130-constructs contained the equivalent K to N and R to Q mutations in the bipartite NLS as described above in the first site (NLS-NQ1), the second site (NLS-NQ2), or both (NLS-NQ1&2) with either HA or HAN epitopes as indicated. The pcDNA3-Rb2/p130-WT and CMV-CD20 constructs which express the wild-type pRb2/p130 without any epitope tags and the IL-2 receptor, respectively, have been described by Claudio et al. *Cancer Res.* 1996 56:2003–2008.

Flow Cytometry Analysis and Colony Formation Assays

Flow cytometry analysis (FACs) was carried out according to procedures described by Claudio et al. *Cancer Res.* 1996 56:2003–2008. Ten micrograms of either pcDNA3, pcDNA3-Rb2/p130-WT, pcDNA3-Rb2/p130-HA, pcDNA3-Rb2/p130-HAN, pcDNA3-Rb2/p130-NLS-NQ1-HA, pcDNA3-Rb2/p130-NLS-NQ1-HAN, pcDNA3-Rb2/p130-NLS-NQ2-HA, pcDNA3-Rb2/p130-NLS-NQ2-HAN, pcDNA3-Rb2/p130-NLS-NQ1&2-HA or pcDNA3-Rb2/p130-NLS-NQ1&2-HAN were co-transfected with 2 µg of CMV-CD20. Eighteen hours after transfection the cells were washed twice with PBS, once with culture medium, and incubated with fresh medium at 37° C. At 48 hours the cells were collected in PBS with 0.1% EDTA and processed for FACs analysis by incubation with the FITC-conjugated anti-CD20 monoclonal antibody (Becton Dickinson, Franklin Lakes, N.J.), fixed in 70% ethanol, stained with propidium iodide, and treated with RNase A as described by Claudioc et al. *Cancer Res.* 1996 56:2003–2008. FACs analysis was performed on a Coulter Elite apparatus, and data from 1×10$^4$ CD20-positive cells were us ed to determine the cell cycle distribution of the selected cells.

Colony formation assay was performed by transfecting triplicate dishes of Saos-2 cells with 10 µg of the indicated DNAs according to the procedure described by Claudio et al. *Cancer Res.* 1994 54:5556–5560. Saos-2 cells were selected with 800 µg/ml G418 for 3 weeks and then stained with 1% methylene blue in 50% ethanol.

Detection of EGFP and EGFP-fusion proteins

Sterile glass cover slips were placed into 10 cm tissue culture dishes and Saos-2 cells were plated 1×10$^6$ cells per dish. Forty-eight hours following transfection with the indicated pEGFP-N1 (Clontech, Palo Alto, Calif.) constructs and fusion proteins, cells were washed 3× with PBS and fixed in freshly made PBS, counterstained with 0.04 mg/ml of propidium iodide in PBS, mounted onto a glass microscope slide with a drop of PBS and sealed with rubber cement. Slides were examined by a Leitz Wetzlar fluorescence equipped microscope; images for illustration purposes were obtained using a cooled charge-coupled device (CCD) camera (Princeton Instruments) The images of the EGFP and EGFP-fusion protein were superimposed to those of the propidium iodide staining.

Example 5

Administration of pRb2/p130 in Cancer Patients

Types of cancer that would be amenable to treatment include nasopharyngeal tumors, lung carcinoma, breast carcinoma, endometrial cancer, glioblastoma, and melanoma. Patient selection would vary with each treatment protocol but could include:

a) treatment of patients with low grade early stage cancers that are surgically resectable (no metastasis)
b) treatment of patients wit h low grade early stage cancers that are not surgically resectable due to location (no metastasis) as the principle therapy and in combination with the optimal chemotherapeutic regimen and/or radiation therapy
c) treatment of patients with high grade intermediate stage cancers that are surgically resectable, in combination with the optimal chemotherapeutic regimen and/or radiation therapy
d) treatment of patients with high grade intermediate stage cancers that are not surgically resectable, in combination with the optimal chemotherapeutic regimen and/or radiation therapy
e) treatment of patients with late stage disease with metastasis in combination with the optimal chemotherapeutic regimen and/or radiation therapy
f) the principle therapy for patients with late stage disease with widespread metastasis The patients with operable tumors would have the tumor area coated with the retrovirus vector containing the pRb2/p130 gene following resection by the surgeon to limit recurrence. The tumor mass could also be injected with the retrovirus prior to surgery. For patients with inoperable tumor masses, injections of the retroviruses would be administered directly into the mass or into arteries that feed the tumor mass. Lung tumors may be treated by inhalation of the adenoviruses. In order to avoid immune activation by the virus, it may be necessary to combine treatment with cyclosporin A exposure prior to virus injection or exposure.

In order to produce the retrovirus for injection to patients, transient transfection is performed. This can be done using the 293T/17 cell line by overnight calcium phosphate treatment using the Promega Profection Mammalian Transfection system on 10 cm dishes seeded the previous day to give a maximum of 70% confluence/plate on the day of transfection. Thirty micrograms of plasmid is used for each transfection. 293T/17 cells are incubated with the precipitates for 15–17 hours, washed twice with medium and fed with 10 ml of fresh medium. The viral supernatant is collected 48 hours after transfection, filtered through 0.45 $\mu$m filters and titered. Viral titer is determined by X-gal staining and by determining the percentage of FITC positive cells following PRINS labeling for the resistance gene carried by the virus after transduction with various dilutions of retroviral supernatant.

What is claimed is:

1. A method of treating a tumor in a patient comprising administering a vector encoding pRb2/p130 directly into the tumor of the patient, wherein said administering inhibits growth of said tumor.

2. The method of claim 1, wherein said tumor is human glioblastoma.

3. The method of claim 1, wherein said tumor is melanoma.

4. The method of claim 1, wherein said tumor is a breast tumor.

5. The method of claim 1, wherein said tumor is a lung tumor.

6. The method of claim 1, wherein said tumor is an endometrial tumor.

7. The method of claim 1, wherein said tumor is stomach carcinoma.

8. The method of claim 1, wherein said vector is an adenoviral vector.

9. The method of claim 1, wherein said vector is a retroviral vector.

* * * * *